US00PP31012P2

(12) United States Plant Patent
Bean et al.

(10) Patent No.: US PP31,012 P2
(45) Date of Patent: Nov. 5, 2019

(54) ***TECOMARIA* PLANT NAMED 'DWOR001'**

(50) Latin Name: *Tecomaria capensis*
Varietal Denomination: DWOR001

(71) Applicant: Charles Andrew de Wet, Johannesburg (ZA)

(72) Inventors: Quinton Bean, Johannesburg (ZA); Charles Andrew de Wet, Johannesburg (ZA)

(73) Assignee: Charles Andrew de Wet, Johannesburg (ZA)

( * ) Notice: Subject to any disclaimer, the term of this patent is extended or adjusted under 35 U.S.C. 154(b) by 0 days.

(21) Appl. No.: 16/350,148

(22) Filed: Oct. 3, 2018

(51) Int. Cl.
*A01H 5/02* (2018.01)

(52) U.S. Cl.
USPC ..... Plt./226

(58) Field of Classification Search
USPC ..... Plt./226
CPC ..... A01H 5/02
See application file for complete search history.

*Primary Examiner* — Annette H Para
(74) *Attorney, Agent, or Firm* — Penny J. Aguirre

(57) ABSTRACT

A new cultivar of *Tecomaria capensis* named 'DWOR001', that is characterized by its compact plant habit, its small plant size, and its flowers that are vivid orange in color.

1 Drawing Sheet

Botanical classification: *Tecomaria capensis*.
Varietal denomination: 'DWOR001'.

CROSS REFERENCE TO RELATED APPLICATIONS

This application is related to U.S. Plant Patent for a plant derived from the same breeding program that is entitled *Tecomaria* Plant Named 'DWOY001' (U.S. Plant patent application Ser. No. 16/350,150), *Tecomaria* Plant Named 'DWPI001' (U.S. Plant patent application Ser. No. 16/350,152), *Tecomaria* Plant Named 'DWRE001' (U.S. Plant patent application Ser. No. 16/350,151), and *Tecomaria* Plant Named 'DWYE001' (U.S. Plant patent application Ser. No. 16/350,149).

BACKGROUND OF THE INVENTION

The present invention relates to a new and distinct cultivar of *Tecomaria capensis* and will be referred to hereafter by its cultivar name, 'DWOR001'. 'DWOR001' represents a new cape honeysuckle, a sub-tropical shrub grown for landscape use.

The new cultivar was derived from a controlled breeding program by the Inventor in Hartebeespoort, North West Province, South Africa. The Inventor made a cross in September of 2013 between unnamed proprietary plants from the Inventor's breeding program as both the female parent and male parent. The Inventor selected 'DWOR001' as a single unique plant amongst the seedlings that resulted from the above cross in August of 2014.

Asexual propagation of the new cultivar was first accomplished by the Inventor by stem cuttings in October 2014 in Hartebeespoort, North West Province, South Africa. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'DWOR001' as a unique cultivar of *Tecomaria capensis*.

1. 'DWOR001' exhibits a compact plant habit.
2. 'DWOR001' exhibits a small plant size.
3. 'DWOR001' exhibits flowers that are vivid orange in color.

The female parent plant of 'DWOR001' differs from 'DWOR001' in having red flowers. The male parent plant of 'DWOR001' differs from 'DWOR001' in having flowers that are dull red in color. 'DWOR001' can also be compared to the *Tecomaria capensis* cultivars 'Lutea' (not patented) and 'Apricot' (not patented) and cultivars from the same breeding program; 'DWOY001', 'DWPI001', 'DWRE001', and 'DWYE001'. 'Lutea' is similar to 'DWOR001' in having a compact plant habit but differs from 'DWOR001' in having yellow flowers. 'Apricot' is similar to 'DWOR001' in flower color but differs from 'DWOR001' in having a larger plant size and in lacking a compact plant habit. 'DWOY001', 'DWPI001', 'DWRE001', and 'DWYE001' are similar to 'DWOR001' in having short plant heights and compact plant habits. 'DWOY001' differs from 'DWOR001' in having flowers that are a blend of orange and yellow in color. 'DWPI001' differs from 'DWOR001' in having pink flowers. 'DWRE001' differs from 'DWOR001' in having red flowers. 'DWYE001' differs from 'DWOR001' in having yellow flowers.

BRIEF DESCRIPTION OF THE DRAWING

The accompanying colored photograph illustrates the overall appearance and distinct characteristics of the new *Tecomaria*, 'DWOR001'. The photograph was taken of one-year-old plants as grown outdoors in 1-gallon containers in Loxley, Ala. The photograph provides a view of the foliage and inflorescences of 'DWOR001'. The colors in the photograph are as close as possible with the digital photography and printing techniques utilized and the color codes in the detailed botanical description accurately describe the new *Tecomaria*.

DETAILED BOTANICAL DESCRIPTION

The following is a detailed description of the new cultivar taken from one-year-old plants as grown outdoors in 1-gallon containers in Loxley, Ala. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Sub-tropical bush; can be deciduous to evergreen depending on climate.

*Plant habit*.—Compact, upright and spreading.

*Height and spread*.—An average of 53 cm in height and 47 cm in spread as grown in a 2-gallon container and reaches 1.5 meters in height and 1.8 m in spread in the landscape.

*Cold hardiness*.—U.S.D.A. Zone 7a.

*Diseases and pests*.—No susceptibility or resistance to diseases or pests has been observed.

*Root description*.—Fine and fibrous, 162D in color.

*Growth rate*.—Moderate to vigorous.

*Propagation*.—Stem cuttings.

*Root development*.—2 to 4 weeks to initiate roots and an average of 6 weeks to fully root as a young plant from a rooted cutting.

Branch description:

*Branch shape*.—Rounded, slightly oval.

*Branching and size*.—An average of 10 lateral branches; average of 28 cm in length and 5.5 mm in width, an average of 4 secondary stems per lateral branch; an average of 11 cm in length and 2.5 mm in width.

*Branch surface*.—New growth; glabrous and semi-glossy with lenticels; about 20 per stem 1.5 cm in length, about 0.3 mm in length, and 155A or 165A in color, mature stems; finely vertically ridged with lenticels; an average of 25 per stem 2.5 cm in length, about 0.75 mm in length, and 165C in color.

*Branch strength*.—Very Strong.

*Branch arrangement*.—Secondary branches primarily opposite.

*Branch aspect*.—Lateral branches primarily upright, secondary branches held at an average angle of 45° from the lateral stems.

*Internode length*.—Average of 1.8 cm.

*Branch color*.—New growth 146B, mature; vertical ridges 197A and 165A.

Foliage description:

*Leaf arrangement*.—Opposite.

*Leaf shape*.—Oblong overall.

*Leaf division*.—Odd-pinnate, typically 7 leaflets (occasionally 3 or 5).

*Leaf size*.—An average of 8 cm in length and 4 cm in width.

*Leaf quantity*.—About 12 per stem 14 cm in length.

*Leaflet base*.—Cuneate or slightly oblique.

*Leaflet apex*.—Acuminate.

*Leaflet venation*.—Pinnate, color: upper surface 144A, lower surface 138B.

*Leaflet shape*.—Elliptic.

*Leaflet margins*.—Serrate.

*Leaflet surface*.—Glabrous, upper surface satiny, lower surface dull.

*Leaflet color*.—New growth upper and lower surface; 144B, mature upper surface; 137A, mature lower surface; 147B.

*Leaflet size*.—An average of 3.3 cm in length and 1.8 cm in width.

*Petiole and rachis*.—Petiole; (from base to lowest leaflet) an average of 2 cm in length and 1 mm in width, rachis; (from lowest leaflet to top of rachis) an average of 4.5 cm in length and 1 mm in length, petiolules; an average of 1 mm in length and width, all are slightly sulcate on upper surface, 144A in color and moderate in strength with glabrous surfaces.

Inflorescence description:

*Blooming period*.—Early to late summer in temperate climates, year around in tropical climates.

*Inflorescence type*.—Terminal panicles, indeterminate.

*Inflorescence size*.—Average of 15 cm in height and 13 cm in width with 18 blooms open, more small buds unopened at apex.

*Flower buds*.—Narrowly obovate in shape and curved slightly downward, an average of 5 cm in length and 1.1 cm in width (at apex), color a blend of 25A to 25D and slightly suffused with N25A at apex.

*Flower fragrance*.—None.

*Lastingness of flowers*.—About 5 days.

*Flower aspect*.—Nearly upright to outward and nodding downward.

*Flower quantity*.—An average of 18 per inflorescence with 3 per peduncle node.

*Flower shape*.—Tubular with petal lobes spreading.

*Flower type*.—Single, tubular (bilabiate in appearance).

*Flower size*.—Average of 6 cm in length and 2.6 cm in diameter.

*Peduncles*.—Oval in shape, an average of 10 cm in length and 3 mm in diameter, strong, held upright, and 137C in color, surface glabrous with lenticels; an average of 8 per 1 cm×3 mm, oblong in shape, average of 0.5 in length, 138D in color, secondary peduncles at peduncle nodes; 5 mm in length and 2.5 mm in width, same shape, color and surface as main peduncles, peduncle leaves; none observed.

*Pedicels*.—Average of 1 cm in length and 1 mm in diameter, held at 15° to vertical, moderately strong and 138B in color.

*Calyx*.—Campanulate in shape, an average of 1 cm in length and 4 mm in diameter, persistent.

*Sepals*.—5, fused with free apices; acuminate apex with mucronate tip, 3 mm in length and 3 mm in width, entire margin, both surfaces smooth and dull, color 144D with thin stripes of 144A on out surface, 144D on inner surface.

*Petals*.—5, lower 60% fused into tube, tube; an average of 4.2 cm in length and 1.2 cm in width (at apex), glabrous and slightly satiny on outer surface, short glistening hairs with ridges due to adnate stamens on inner surface, color on outer surface a blend 25A to 25C and N25B, color inner surface a blend of 25A and 26B with filaments of adnate stamens 25D and very base 14C, lobes; oblong in shape, margin entire and very slightly wavy, apex obtuse, base fused to tube, color outer and inner surface a blend 25A to 25C and N25B, 2 cm in length and 1 cm in width, upper 2 petals; lower 50% fused together, held upright and slightly reflexed, lower 3 petals; held outward and strongly reflexed, corona not persistent.

Reproductive organs:

*Gynoecium.*—1 pistil, about 6 cm in length, style is an average of 5.8 cm in length, and 154B in color, stigma is club-shaped, 1.5 mm in diameter, and 154A in color, ovary is oblong in shape, 4 mm in length and 154A in color.

*Androecium.*—5 stamens, anthers are dorsifixed, 2-lobed, narrow oblong in shape, lobes 3 mm in length and 21D in color, filaments are an average of 5 cm in length and 25D in color and blending to 11A at apex with lower 40% adnate to petals, pollen is moderate in quantity and 21A in color.

*Fruit and seed.*—No fruit or seed production has been observed to date.

It is claimed:

1. A new and distinct cultivar of *Tecomaria* plant named 'DWOR001' as herein illustrated and described.

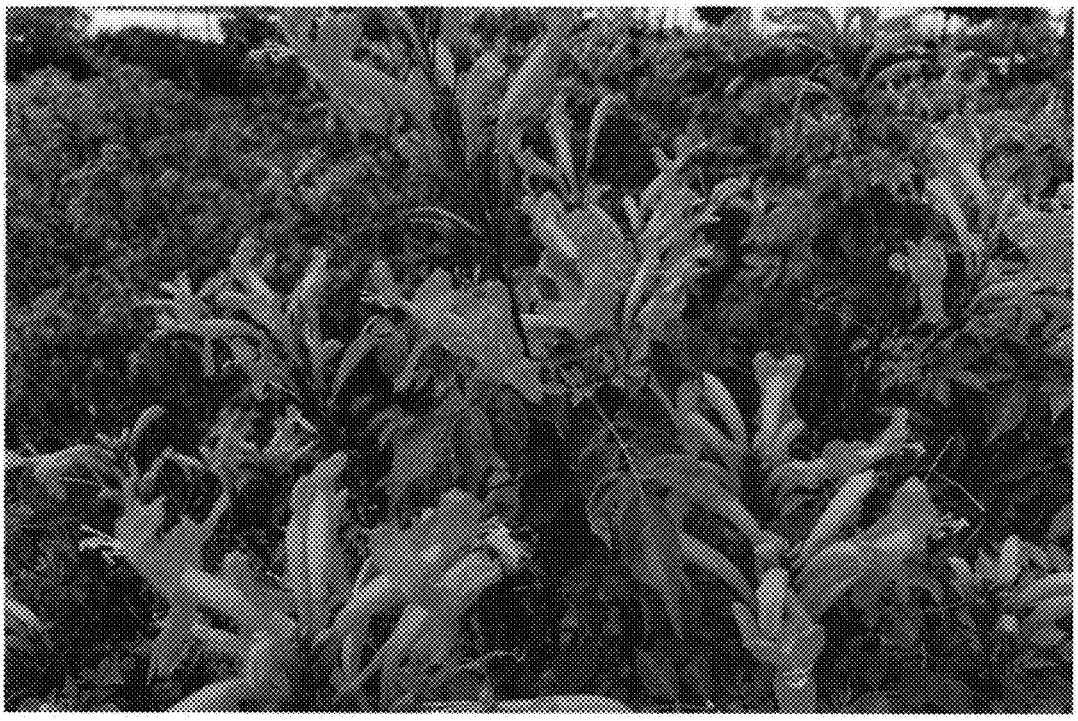

* * * * *